United States Patent
Ng et al.

(10) Patent No.: US 10,302,650 B2
(45) Date of Patent: May 28, 2019

(54) HIGH-THROUGHPUT FLUORESCENCE POLARIZATION MICROORGANISM SCREENING ASSAY

(71) Applicant: THE TRUSTEES OF COLUMBIA UNIVERSITY IN THE CITY OF NEW YORK, New York, NY (US)

(72) Inventors: Yao Zong Ng, Singapore (SG); Pedro Alexis Baldera Aguayo, New York, NY (US); Virginia W. Cornish, New York, NY (US); Ehud Herbst, New York, NY (US)

(73) Assignee: THE TRUSTEES OF COLUMBIA UNIVERSITY IN THE CITY OF NEW YORK, New York, NY (US)

(*) Notice: Subject to any disclaimer, the term of this patent is extended or adjusted under 35 U.S.C. 154(b) by 0 days.

(21) Appl. No.: 16/008,777

(22) Filed: Jun. 14, 2018

(65) Prior Publication Data

US 2018/0299457 A1 Oct. 18, 2018

Related U.S. Application Data

(63) Continuation of application No. PCT/US2016/068513, filed on Dec. 23, 2016.

(Continued)

(51) Int. Cl.
*G01N 33/58* (2006.01)
*G01N 21/64* (2006.01)
(Continued)

(52) U.S. Cl.
CPC .......... *G01N 33/582* (2013.01); *C12N 15/10* (2013.01); *C12N 15/1086* (2013.01); *C12Q 1/68* (2013.01);
(Continued)

(58) Field of Classification Search
CPC .... C12N 15/10; C12N 15/1086; G01N 21/64; G01N 33/56944; G01N 33/582;
(Continued)

(56) References Cited

U.S. PATENT DOCUMENTS

| | | |
|---|---|---|
| 6,649,595 B2 | 11/2003 | Clackson et al. |
| 2005/0070005 A1 | 3/2005 | Keller |
| 2005/0208613 A1 | 9/2005 | Qin |

FOREIGN PATENT DOCUMENTS

WO 2001/032858 5/2001

OTHER PUBLICATIONS

Dietrich et al. (Annu. Rev. Biochem., 2010, 79:563-90) (Year: 2010).*

(Continued)

*Primary Examiner* — Jeremy C Flinders
(74) *Attorney, Agent, or Firm* — Baker Botts L.L.P.

(57) ABSTRACT

The present disclosure provides a high-throughput fluorescence polarization microorganism screening assay for a metabolite produced by a microorganism. The metabolite is detected using competition with a fluorescent reporter for a receptor that binds both the metabolite and the reporter. The present disclosure further provides materials used in such an assay, a kit for such an assay, an isolated microorganism identified using such an assay, and culture conditions identified using such an assay.

44 Claims, 11 Drawing Sheets

Related U.S. Application Data

(60) Provisional application No. 62/387,306, filed on Dec. 23, 2015.

(51) Int. Cl.
*C12N 15/10* (2006.01)
*G01N 33/569* (2006.01)
*C40B 40/02* (2006.01)
*C12Q 1/68* (2018.01)
*G01N 33/542* (2006.01)

(52) U.S. Cl.
CPC ............ *C40B 40/02* (2013.01); *G01N 21/64* (2013.01); *G01N 33/542* (2013.01); *G01N 33/569* (2013.01); *G01N 33/56944* (2013.01)

(58) Field of Classification Search
CPC ...... G01N 33/542; G01N 33/569; C12Q 1/68; C40B 40/02
See application file for complete search history.

(56) References Cited

OTHER PUBLICATIONS

International Search Report and Written Opinion for International application No. PCT/US2016/068513, dated Mar. 9, 2017, 8 pages.

Bollini et al., "High-Throughput Fluorescence Polarization Method for Identification of FKBP12 Ligands," J. Biol. Screen 7(6):526-530 (2002).

Clackson et al., "Redesigning an FKBP-ligand interface to generate chemical dimerizers with novel specificity," PNAS USA 95:10437-10442 (1998).

De Felipe et al., "Correlation between Ligand-Receptor Affinity and the Transcription Readout in a Yeast Three Hybrid System," Biochemistry 43:10353-10363 (2004).

Duetz, "Microtiter plates as mini-bioreactors: miniaturization of fermentation methods," Trends Microbiol 15(10):469-475 (2007).

Kozany et al., "Fluorescent Probes to Characterise FK506-Binding Proteins," Chembiochem 10:1402-1410 (2009).

Minas et al., "Streptomycetes in micro-cultures; Growth, Production of Secondary Metabolites, and Storage and Retrieval in the 96-well format," Antonie Van Leeuwenhoek 78:297-305 (2000).

Xu et al., "A high-throughput method for screening of rapamycin-producing strains of *Streptomyces hygroscopicus* by cultivation in 96-well microtiter plates," Biotechnol Lett 27:1135-1140 (2005).

Zhang et al., "A Simple Statistical Parameter for Use in Evaluation and Validation of High Throughput Screening Assays," Journal of Biomolecular Screening 4(2):67-73 (1999).

Zhu, "A Rapid, Small-Scale Method for Improving Fermentation Medium Performance," Thesis, The University of Waikato: Hamilton, New Zealand (2007).

\* cited by examiner

HIGH-THROUGHPUT FLUORESCENCE POLARIZATION MICROORGANISM SCREENING ASSAY

PRIORITY CLAIM

The present application is a continuation application of PCT Application PCT/US2016/068513, filed Dec. 23, 2016, and titled "FLUORESCENCE POLARIZATION MICROORGANISM SCREENING ASSAY," which claims priority to U.S. Provisional Patent Application Ser. No. 62/387,306, filed Dec. 23, 2015 and titled "FLUORESCENCE POLARIZATION ASSAY FOR HIGH-THROUGHPUT SCREENING OF FK506 PRODUCED IN MICROTITER PLATES," which is incorporated by reference herein in its entirety.

GOVERNMENT SUPPORT CLAUSE

This invention was made with government support under grant GM096064 awarded by the National Institutes of Health. The Government has certain rights in this invention.

1. TECHNICAL FIELD

The present disclosure relates to a high-throughput fluorescence polarization microorganism screening assay for a metabolite produced by a microorganism, as well as materials used in such an assay, a kit for such an assay, an isolated microorganism strain identified using such an assay, and culture conditions identified using such an assay.

2. BACKGROUND

High-throughput screening has been used to successfully detect single protein changes or other simple changes in microorganisms. Microorganisms that produce a particular metabolite or are high-producers of a particular metabolite, such as metabolically engineered microorganisms, tend to exhibit combinatorial optimization involving multi-gene pathways and interacting cellular networks, which simultaneously perturb multiple cellular pathways to achieve an increase in a metabolite. Screening for metabolites resulting in such complex changes is not compatible with existing high-throughput screening technologies. Instead, microorganisms producing a particular metabolite tend to be screened using expensive, slow, or limited-target methods, such as small molecule metabolite detection via gas/liquid chromatography, fluorescence-activated cell sorting, or even growth selection on agar plates. Other screening methods have relied on complex binding and signal-transduction functions, which have not proven readily adaptable to a variety of targets and contexts.

As a result, the number of microorganisms available to produce useful metabolites is limited. Yet, such organisms may be identified from samples and metabolically engineered microorganisms may be produced quite readily using any of numerous different technologies that are able to produce large strain libraries, often each including more than $10^6$ different strains. If these various microorganisms could be screened in a high-throughput assay for a given metabolite, high-producing strains as well as high-producing culture conditions could be rapidly identified, the costs of such products could be lowered and availability increased. Furthermore, new metabolites with desirable functions may be identified.

3. SUMMARY

The disclosure provides a method of high-throughput fluorescence polarization microorganism screening.

The method, when used to designate high-producing or low-producing microorganisms, includes culturing a plurality of microorganism strains that produce a metabolite in a plurality of separate compartments to produce a plurality of samples; adding a receptor and fluorescent reporter to the plurality of samples obtained from the plurality of compartments; detecting fluorescence polarization of the reporter in the plurality of samples in a multi-compartment fluorescence polarization assay device, wherein fluorescence polarization of the reporter correlates inversely with a concentration of the metabolite in any given sample because the metabolite competes with the fluorescent reporter to bind to the receptor and binding of the fluorescent reporter to the receptor increases fluorescence polarization; calculating concentration of the metabolite in at least a portion of the plurality of samples; and designating at least one of the plurality of microorganism strains as high-producing or low-producing based on the calculated concentration of metabolite for at least one sample.

The method, when used to designate high-producing or low-producing culture conditions, includes culturing a microorganism strain that produces a metabolite under plurality of different culture conditions in a plurality of separate compartments to produce a plurality of samples; adding a receptor and fluorescent reporter to the plurality of samples obtained from the plurality of compartments; detecting fluorescence polarization of the reporter in the plurality of samples in a multi-compartment fluorescence polarization assay device, wherein fluorescence polarization of the reporter correlates inversely with a concentration of the metabolite in any given sample because the metabolite competes with the fluorescent reporter to bind to the receptor and binding of the fluorescent reporter to the receptor increases fluorescence polarization; calculating concentration of the metabolite in at least a portion of the plurality of samples; and designating at least one of the plurality of culture conditions as high-producing or low-producing based on the calculated concentration of metabolite for at least one sample.

The method further includes a combined high-throughput fluorescence polarization microorganism screening assay used to designate both high-producing and low-producing microorganisms and high-producing and low-producing culture conditions in the same assay.

Any of the above assays may have the following additional features, which may further be combined with one another unless clearly mutually exclusive:

a) the plurality of separate compartments may include wells on a multi-well plate;

b) the multi-compartment fluorescence polarization assay device may include a multi-well plate;

c) the plurality of separate compartments used in culturing may be the same as a plurality of compartments in the multi-compartment fluorescence polarization assay device used in detecting fluorescence polarization;

d) the multi-compartment fluorescence polarization assay device comprises more compartments than the plurality of separate compartments used in culturing;

i) the plurality of samples may include duplicate samples obtained from the same compartment used in culturing, and each of the duplicate samples may be located in a separate compartment of the multi-compartment fluorescence polarization assay device;

ii) at least a portion of the plurality of samples may be diluted to different dilutions, and each dilution may be located in a separate compartment of the multi-compartment polarization assay device;

iii) at least two different concentrations of receptor or fluorescent reporter may be added to different samples from the same compartment used for culture in at least a portion of the plurality of samples, and each dilution may be located in a separate compartment of the multi-compartment polarization assay device;

e) the method may further include varying a concentration of the receptor or varying a concentration of the fluorescent reporter to detect a different concentration of metabolite or a different metabolite;

f) the microorganism includes a bacteria;

g) the microorganism includes a fungus;

h) the microorganism includes a yeast;

i) the microorganism includes an algae;

j) the microorganism may be present as individual cells small, unorganized clumps of cells due to a stage in the microorganism's life cycle or due to culture conditions;

k) the microorganism may include a recombinant microorganism;

l) the microorganism may include a non-recombinant microorganism;

m) the microorganism may include a metabolically engineered microorganism;

i) the method may further include producing the plurality of metabolically engineered microorganism strains by subjecting a microorganism to ultraviolet radiation;

n) the method may further include assaying microorganism growth in at least a portion of the plurality of samples;

i) the method may further include assaying microorganism growth in a separate multi-compartment device than the multi-compartment fluorescence polarization assay device;

ii) designating at least one of the plurality of microorganism strains (or culture conditions) as high-producing or low-producing may also be based on the assayed microorganism growth;

iii) assaying microorganism growth may include adding a growth detection agent to a plurality of growth samples corresponding to the plurality of samples, then detecting the growth detection agent in the plurality of growth samples;

iv) the method may include generating a standard curve for use in assaying microorganism growth.

o) the method may further include treating the plurality of samples to render the metabolite accessible to bind to the receptor, for example by freeze-thaw methods, by adding solvent, and/or by adding a detergent;

p) the receptor may include a protein;

q) the receptor may include a DNA-based molecule or an RNA-based molecule;

r) the fluorescent reporter may include a small molecule able to bind to the receptor and a fluorescent molecule i) the fluorescent molecule may include a fluorescein, a rhodamine, or a cyanine.

s) the method may further include generating a standard curve correlating metabolite concentration and fluorescence polarization for the metabolite for use in calculating concentration of the metabolite;

t) at least $10^2$ separate wells each containing one of the plurality of microorganism strains may be assayed per day;

u) the metabolite and fluorescent reporter may have binding affinities for the reporter within one order of magnitude from one another;

v) the metabolite or the fluorescent reporter or both may have an equilibrium dissociation constant ($K_d$) with respect to the receptor of less than 1 mM;

w) the method of high-throughput fluorescence polarization microorganism screening may have a Z' score of at least 0.70;

w) the reporter may include FKBP12, the fluorescent reporter may include FK506 (tacrolimus), rapamycin (sirolimus), meridamycin, SLF, their analogs, and any combinations thereof;

i) the metabolite may include FK506 (tacrolimus), rapamycin (sirolimus), meridamycin, SLF, their analogs, and any combinations thereof;

ii) the microorganism may include *Streptomyces tsukubaensis*.

x) the receptor may include *E. coli* dihydrofolate reductase (eDHFR), the fluorescent reporter may include trimethoprim (TMP), it analogs, and any combinations thereof;

i) the metabolite may include trimethoprim (TMP), it analogs, and any combinations thereof;

y) the receptor may include tetracycline receptor (TetR), and the fluorescent reporter may include a TAN molecule, its analogs, and any combinations thereof;

i) the metabolite may include a TAN molecule, its analogs, and any combinations thereof;

z) the receptor comprises a penicillin binding protein; 5HT; adenine transferase; estrogen receptor; cyclophilin; adiponectin; cannabinoid; domapine; or asparate transcarbamylase, and the fluorescent reporter may include, respectively penicillin, its analogs, and any combinations thereof; serotonin, its analogs, and any combinations thereof; adenine, its analogs, and any combinations thereof; estradiol, its analogs, and any combinations thereof; cyclosporin A (CsA), its analogs, and any combinations thereof; matairesinol, arctiin, gramine, their analogs, and any combinations thereof; clonazepam, phenobarbital, their analogs, and any combinations thereof; tetrandrine its analogs, and any combinations thereof; and adenosine triphosphate (ATP) its analogs, and any combinations thereof;

i) the metabolite may include, respectively penicillin, its analogs, and any combinations thereof; serotonin, its analogs, and any combinations thereof; adenine, its analogs, and any combinations thereof; estradiol, its analogs, and any combinations thereof; cyclosporin A (CsA), its analogs, and any combinations thereof; matairesinol, arctiin, gramine, their analogs, and any combinations thereof; clonazepam, phenobarbital, their analogs, and any combinations thereof; tetrandrine its analogs, and any combinations thereof; and adenosine triphosphate (ATP) its analogs, and any combinations thereof;

aa) at least two of the plurality of culture conditions may includedifferent culture media, different culture supplements, different culture temperatures, different culture atmospheres, different culture motions, such as shaking, different durations of culture, and any combinations thereof.

The present disclosure further includes a kit for a high-throughput fluorescence polarization microorganism screening assay including at least two materials used to perform any of the above methods.

The present disclosure further includes a microorganism and/or a culture condition designated as high-producing using any of the above methods.

4. BRIEF DESCRIPTION OF THE DRAWINGS

For a more complete understanding of the present invention and its features and advantages, reference is now made to the following description, taken in conjunction with the accompanying drawings, in which like numerals refer to like features, and in which.

Figure 7:
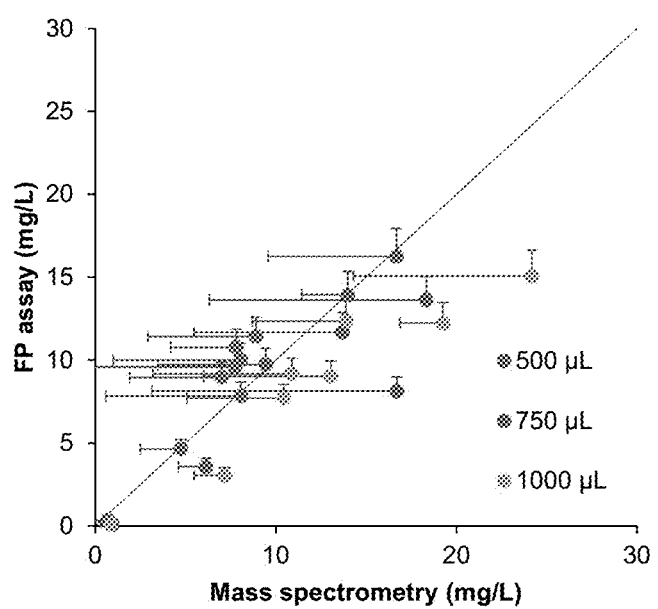
Figure 8:
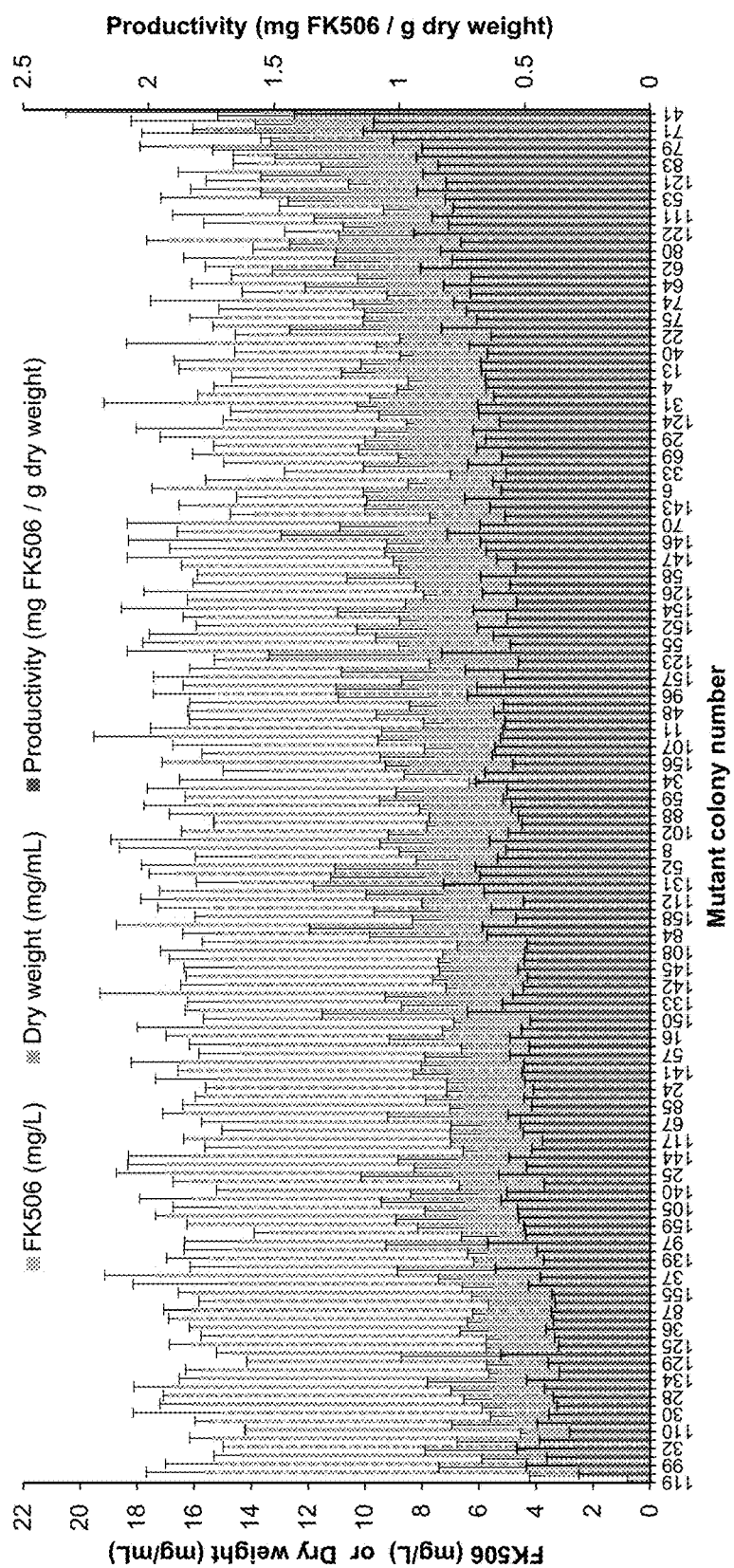
Figure 9:
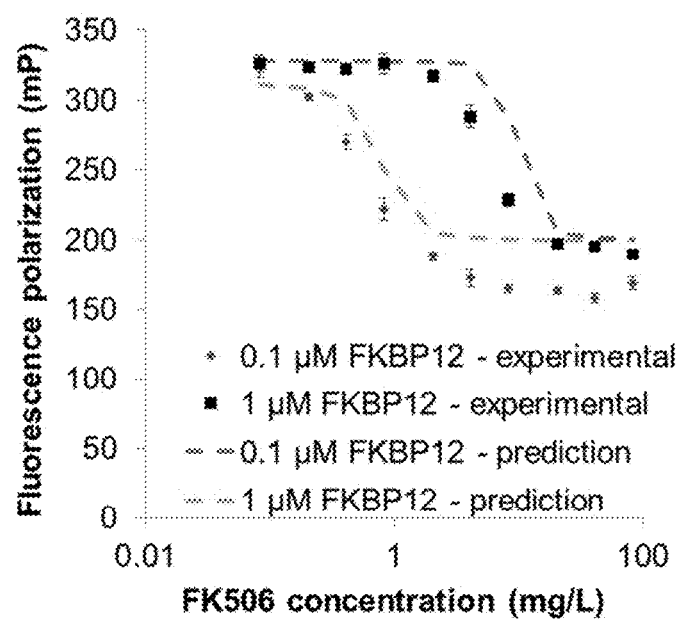
Figure 10:
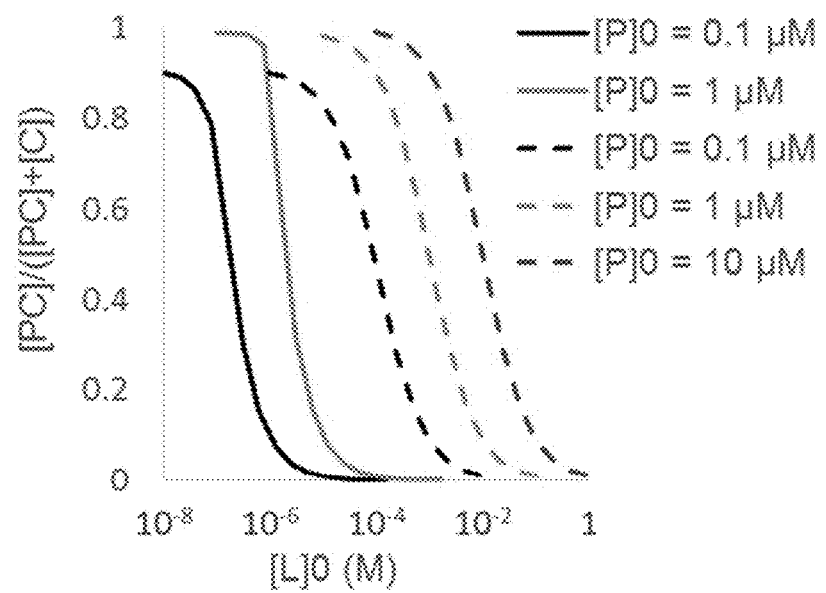
Figure 11:
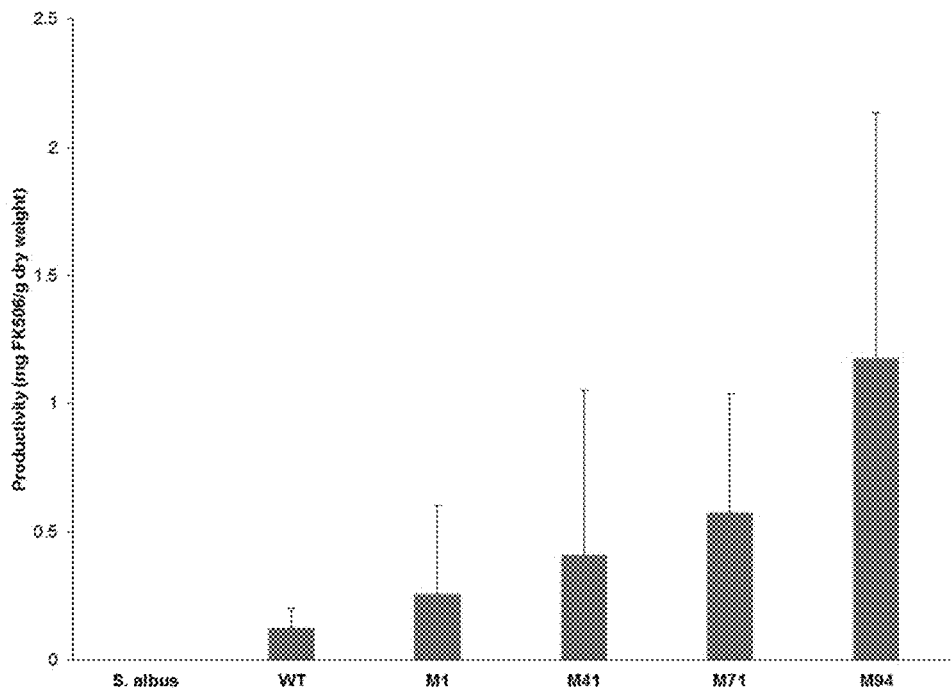
Figure 12:
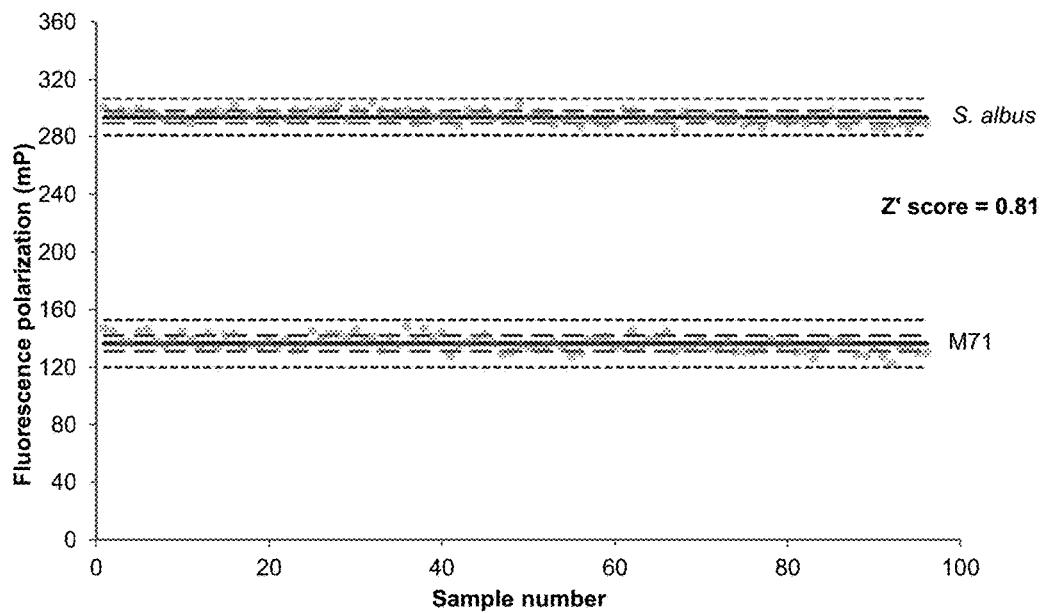
Figure 13:
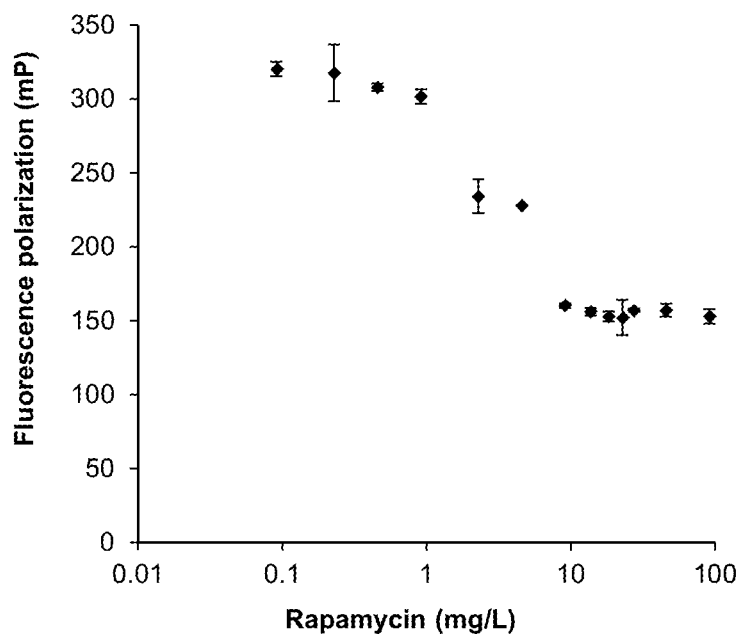
Figure 14:
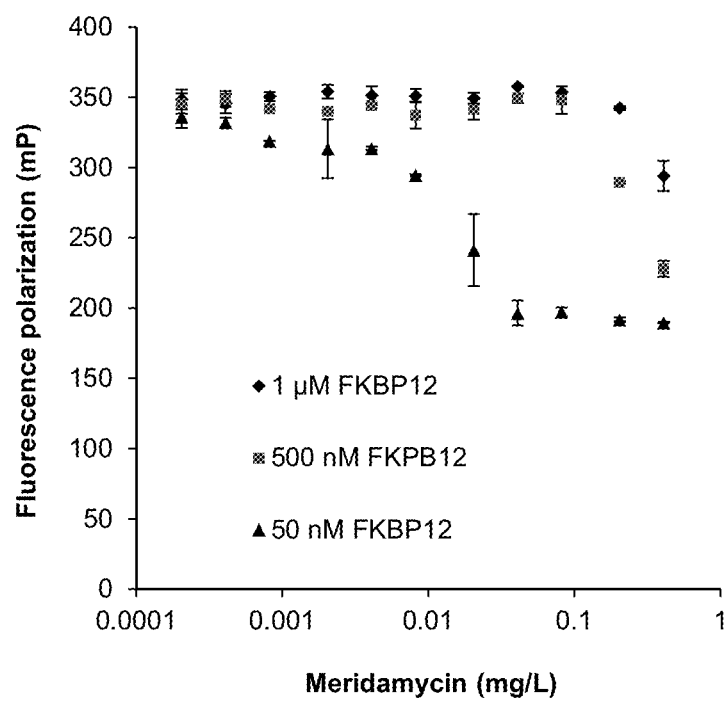
Figure 15:
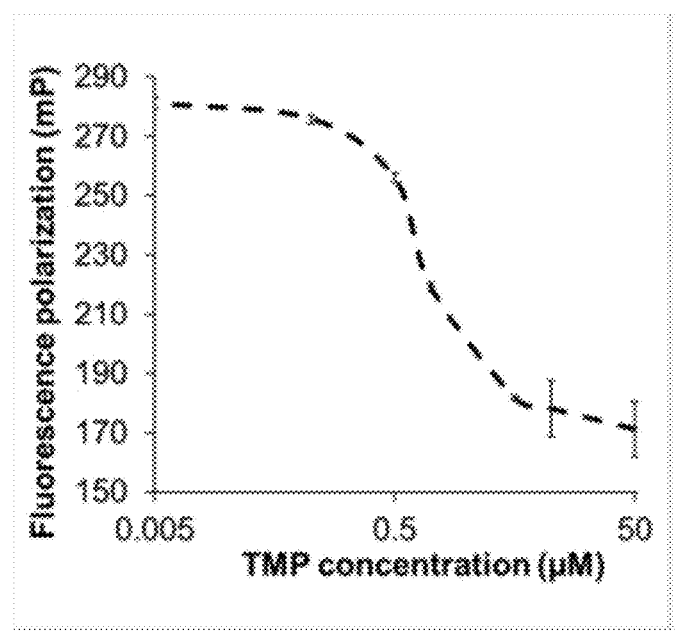
Figure 16:
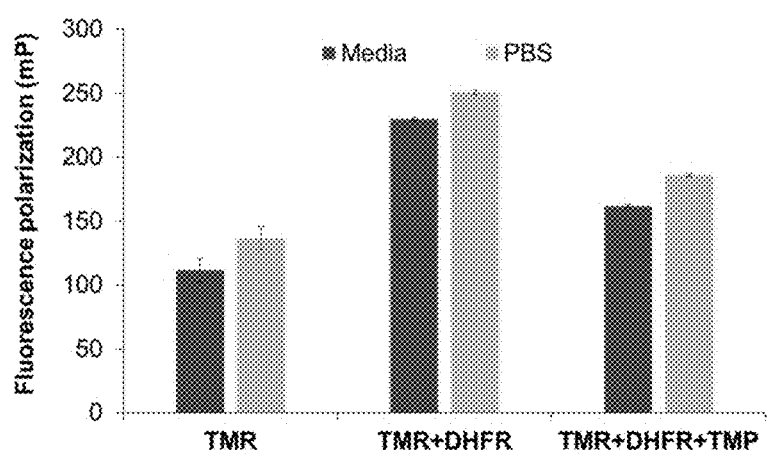
Figure 17:
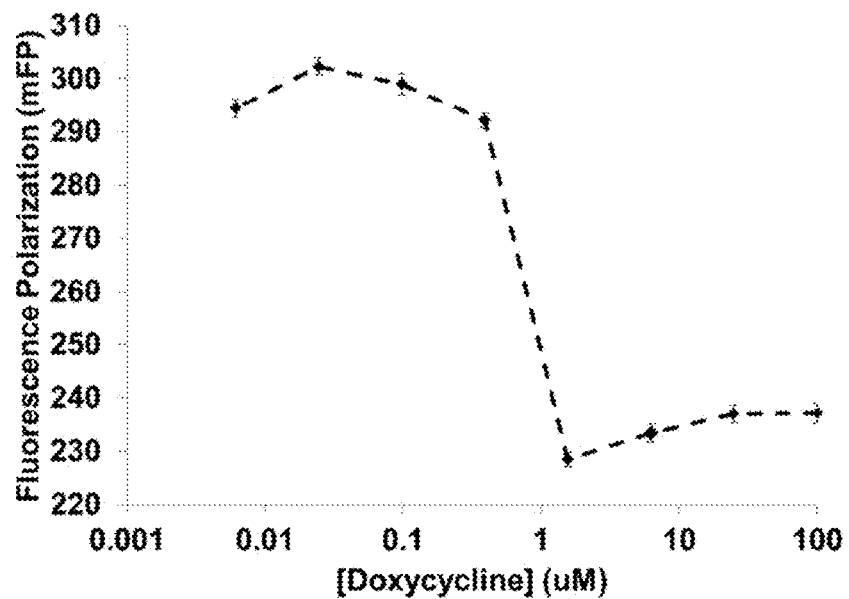
Figure 18:
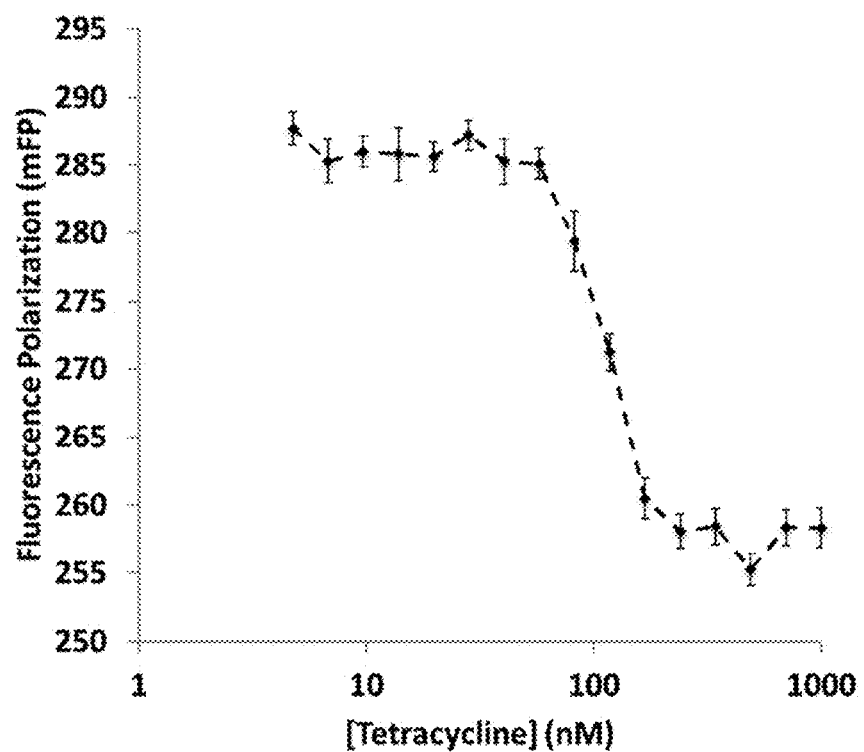
Figure 19:
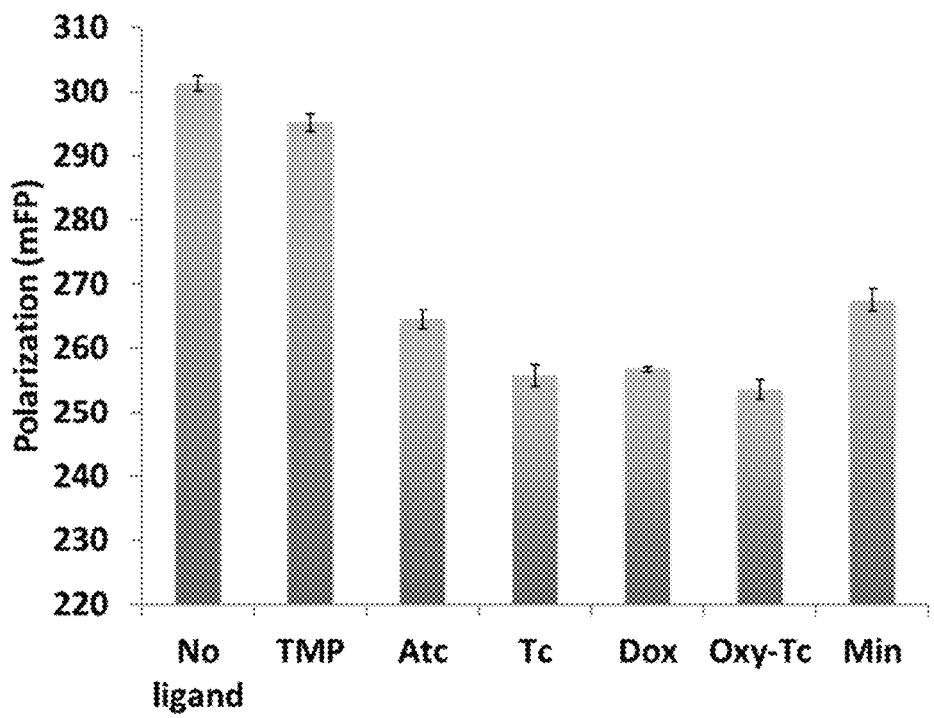
Figure 20:
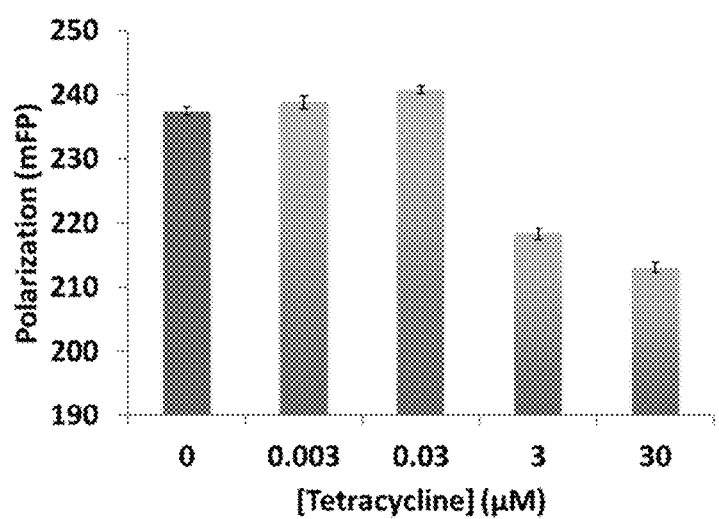

FIG. 7 is a correlation chart for mass spectrometry and fluorescent polarization assay measurements of FK506 concentrations for various metabolically engineered microorganism strain samples; for clarity, only the left error bars (mass spectrometry measurements) and top error bars (FP measurements) are shown; all data points are the mean of 4 wells and all error bars represent the standard deviation from 4 wells;

FIG. 8 is graph of FK506 metabolite concentration and productivity in culture samples of metabolically engineered microorganisms from different wells of a culture multi-well plate (bottom green bars, y-axis on the right) arranged in ascending order of productivity from left to right; only half of the mutated strains are labelled; the bright red bar represents the average of 16 wells of a non-mutated strain; for all other mutant strains, bars represent the average of 2 wells grown in different plates; the amount of FK506 present (middle yellow bars, y-axis on the left) and dry weight of cells (upper green bars, y-axis on the left) are also shown; error bars represent the standard deviation for the 2 replicates; all FK506 values were background subtracted based on wells containing culture media alone;

FIG. 9 is a graph of actual fluorescence polarization values corresponding to various FK506 concentrations detected by a fluorescence polarization assay and predicted fluorescence polarization values corresponding to various FK506 concentrations;

FIG. 10 is a graph of the expected effects on the dynamic range of a fluorescence polarization assay of changing receptor concentration and KDPL (the $K_d$ between the receptor and the metabolite); The $K_d$ between the receptor and the fluorescent reporter is KDPC=$[C]_0$=10 nM; the solid line represents KDPL=10 nM; the dashed line represents KDPL=10 μM;

FIG. 11 is a graph of the shake flask productivity of metabolically engineered microorganisms identified as high-producing using a high-throughput fluorescence polarization microorganism screening assay; all bars represent the mean of 9 replicates (3 separate trials using 3 flasks per mutant) and error bars represent one standard deviation; all FK506 values were background subtracted based on flask culture media alone;

FIG. 12 is a graph of results used to calculate a Z' score for a fluorescence polarization assay for FK506; the figure shows the mean of the controls (continuous black line), one standard deviation (long dashes) and 3 standard deviations (short dashes) from the mean;

FIG. 13 is a fluorescence polarization assay standard curve for rapamycin;

FIG. 14 is a fluorescence polarization assay standard curve for meridamycin;

FIG. 15 is a graph of trimethoprim detection via a fluorescence polarization assay at concentrations of 0.5 μM to 5 μM;

FIG. 16 is a graph of trimethoprim detection in spiked yeast growth media via a fluorescence polarization assay;

FIG. 17 is graph of doxycycline detection via a fluorescence polarization assay; all wells were assayed in triplicate with error bars representing standard errors;

FIG. 18 is graph of tetracycline detection via a fluorescence polarization assay; all wells were assayed in triplicate with error bars representing standard errors;

FIG. 19 is graph of tetracycline, doxycycline, anhydrotetracycline, oxytetracycline, minocycline detection via a fluorescence polarization assay; all wells were assayed in triplicate with error bars representing standard errors; and FIG. 20 is graph of tetracycline detection via a fluorescence polarization assay in a spiked *Streptomyces lividans* (*S. lividans*) culture; all wells were assayed in triplicate with error bars representing standard errors.

5. DETAILED DESCRIPTION

The present disclosure provides a high-throughput fluorescence polarization microorganism screening assay for a metabolite produced by a microorganism, such as a metabolically engineered microorganism. The screening assay may be used to select a microorganism strain for use in producing the metabolite. The present disclosure further includes materials used in the high-throughput fluorescence polarization microorganism screening assay, a kit for such an assay, and an isolated microorganism strain identified using such an assay, including an a metabolically engineered microorganism strain. Furthermore, the present disclosure may be used to identify high-producing microorganisms for known metabolites or their analogs, to identify new analogs of known metabolites or new metabolites, to metabolically engineer high-producing microorganisms for metabolites, to screen culture conditions, and to detect new metabolites.

A high-throughput fluorescence polarization microorganism screening assay as disclosed herein may generally be used to detect metabolite production in culture in a plurality of compartments by any microorganism that may be cultured on such as plate. Detection in a fluorescence polarization assay may generally be via any receptor able to bind at least the metabolite in the presence of culture media or substantial components of culture media. Detection may not require the use of highly purified detection media with a specific chemical composition; rather, it may flexibly occur in culture media or minimally purified culture media whose chemical composition may vary widely. The fluorescent reporter may be fluorescent molecule/small molecule complex that competes with a metabolite for binding to a reporter, including a fluorescent derivative of the metabolite, such as a fluorescent molecule/metabolite complex or a fluorescent derivative of a small molecule similar to the metabolite.

Figure 1:
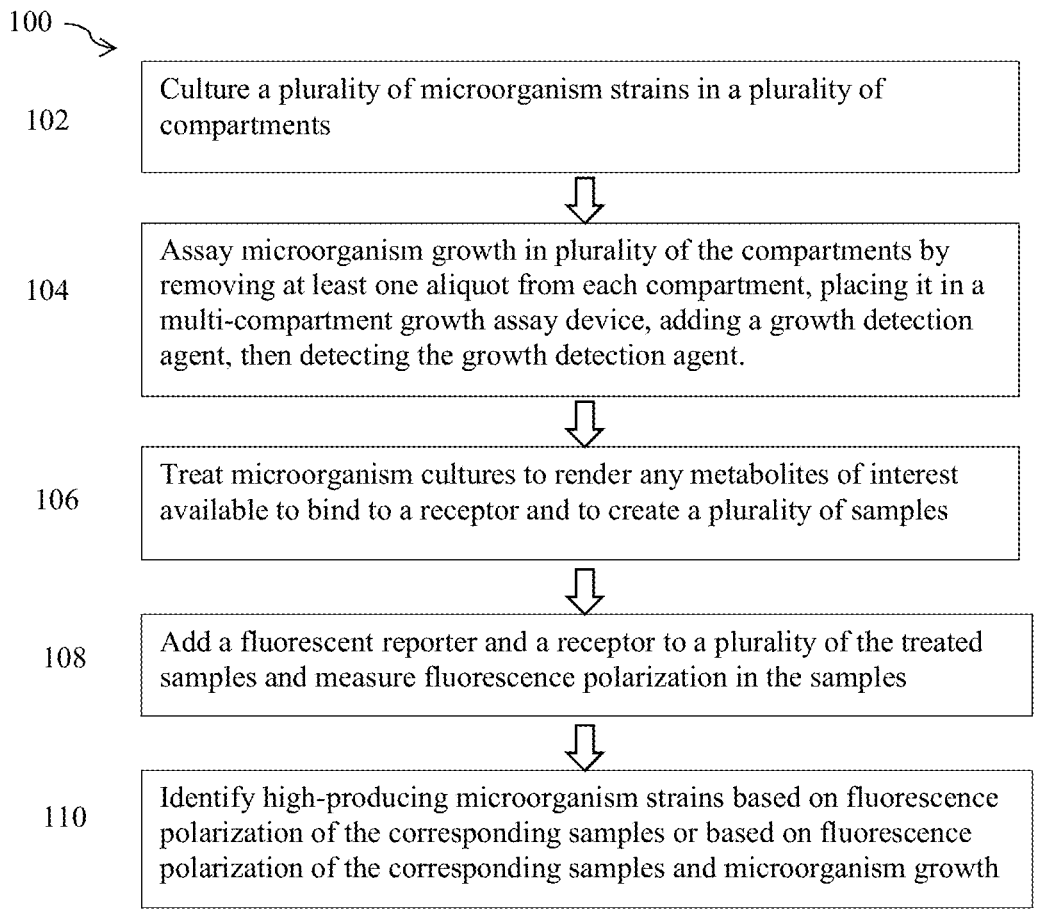
FIG. 1 is a flow chart of a high-throughput fluorescence polarization microorganism screening assay for metabolites.

Referring now to FIG. 1, which is a flow chart of a high-throughput fluorescence polarization microorganism screening assay 100 usable to detect a metabolite, in step 102 a plurality of microorganism strains, such as metabolically engineered microorganism strains, are cultured in a plurality of compartments. Typically, only one microorganism strain will be present per compartment.

The particular metabolite detected in the high-throughput fluorescence polarization microorganism screening assay may be any small molecule produced by a microorganism and able to bind a receptor. In some instances, the metabolite may be secreted into and/or be soluble in a culture medium in which the microorganism is being cultured. In other instances, it may be substantially not secreted and may remain substantially within the cells of the microorganism, or it may be substantially not soluble even if secreted. The metabolite as detected by the high-throughput fluorescence polarization microorganism screening assay may be the metabolite as produced by the microorganism, or it may be a derivative that has been chemically modified to allow or improve its detection.

The microorganism may be any microorganism that produces a particular metabolite that is detected in the high-throughput fluorescence polarization microorganism screening assay. For example, the microorganism may be a bacteria, a fungus, such as a yeast, or an algae. The microorganism may also include an organism present as individual cells or small, unorganized clumps of cells due to a stage in the microorganism's life cycle or due to culture conditions. For example, the microorganism may be a Dictyosteliida or other slime mold, a plant cell or small plant callus, or an animal cell.

The microorganism may be a recombinant microorganism able to express an exogenous nucleic acid encoding one or more proteins, particularly enzymes, that produce the metabolite or a metabolite precursor. The microorganism may also be a non-recombinant microorganisms that expresses an endogenous nucleic acid encoding one or more proteins, particularly enzymes, that produce the metabolite or a metabolite precursor.

If the microorganism is a metabolically engineered microorganism, it may exhibit a production level for the metabolite higher than a non-metabolically engineered microorganism. A metabolically engineered microorganism may be derived from a recombinant or a non-recombinant microorganism.

A high-throughput fluorescence polarization microorganism screening assay as described herein may be used to select high-producing microorganisms, whether non-recombinant or recombinant and not metabolically engineered or metabolically engineered.

If the microorganism is a metabolically engineered microorganism, the plurality of microorganism strains used in this step 102 may be produced using any suitable method. In particular, they may be produced using a method that results in at least $10^2$ different strains of microorganisms, at least $10^4$ different strains of microorganisms, or at least $10^6$ different strains of microorganisms. For instance, a suspension of microorganisms, such as a suspension of a single strain of microorganisms, may be irradiated with ultraviolet light at a wavelength and intensity and for a length of time sufficient to cause one or more mutations in a plurality of the suspension of microorganisms, resulting in a plurality of metabolically engineered microorganism strains in suspension. This suspension may be cultured to allow the microorganisms to recover, then plated on agar at a density that allows the growth of individual colonies representing different strains of the metabolically engineered microorganisms. Single colonies may then be picked and each colony cultured in a separate well of the multi-well plate. Alternatively, after the suspension is cultured to allow the microorganisms to recover, it may be diluted and placed in the separate wells of the multi-well plate. The dilution may be such that each of the separate wells is expected to contain only one microorganism strain. Other alternative methods expected to result in one strain per well of the multi-well plate may also be used. Similar methods may be used to obtain one strain per well from a culture of non-metabolically engineered microorganisms.

The compartment may be a compartment in which the microorganisms can be cultured. The compartment may be defined by a rigid, physical structure, such as a well in a multi-well plate, for example a 96-well, deep-well plate. The compartment may also be a compartment defined by a flexible physical separation, such as a bead of hydrophobic fluid, such as oil, in a hydrophilic fluid, such as an aqueous fluid, or a bead of hydrophilic fluid in a hydrophobic fluid. The plurality of compartment may be located in one physical entity, such as one multi-well plate, or in separate physical entities, such as a series of multi-well plates. Although a multi-well plate is frequently used herein to describe examples of microorganism culture, other compartments may typically be used in the place of a multi-well plate.

The plurality of compartments used for culture may be selected to be of similar throughput as the multi-well plates or other multi-compartment assay devices used for the fluorescence polarization assay as well as any other multi-well plates or multi-compartment devices whose contents are later transferred into the multi-well plates or multi-compartment assay devices used for the fluorescence polarization assay. For example, 96-well plates may be used for culture and also for the fluorescence polarization assay. As another example, 96-well plates may be used for culture, and a higher well number plate, such as a 384-well plate may be used for the fluorescence polarization assay. The use of a higher well number plate for the fluorescence polarization assay than for culture allows for multiple assays of the same sample, for example to obtain results for duplicate assays or to test the same sample at different dilutions or with different concentrations of receptor or fluorescent reporter simultaneously, which may further speed up the high-throughput screening.

Filamentous microorganisms are difficult to culture on multi-well plates because oxygen transfer rates quickly become limiting for cell growth and metabolite production. However, deep well plates or other plates with square shapes allow the growth of filamentous microorganisms, particularly when combined with a high-frequency shaker, a large shaking orbit, tilted rotation, and/or small culture volumes as compared to well volume, such as less than 50%, less than 20%, or less than 10% of well volume. Accordingly, a microorganism screened using a high-throughput fluorescence polarization microorganism screening assay as described herein may, in particular, be a filamentous microorganism In step 104, which is optional, microorganism growth may be assayed by removing at least one aliquot from each well, placing it in another multi-well plate or multi-compartment growth assay device, and adding a growth detection agent, such as methylene blue to the aliquot, then detecting the growth detection agent, such as by using spectroscopy. Growth may also be assayed by measuring optical density or by other methods. The growth may be expressed in any of a variety of formats, but will typically be convertible to a cell density measurement, representing the density of cells in the culture well. The multi-well plate or multi-compartment growth assay device used for this microorganism growth assay may have at least as many compartments as the multi-well plate or plurality of compartments used for culture. It may also have more compartments to allow for duplicate tests of the same sample.

In step 106, which is optional, the microorganism strain cultures are treated to render any metabolites of interest available to bind to a receptor. If the metabolites of interest are already available to bind to the receptor, then such treatment is not needed. This step, if present, may be performed before or after step 104, also if present, in which microorganism growth is assayed. If the growth detection agent provides more accurate results before the microorganism strain cultures are treated, then this step will typically be performed prior to step 104, or at least prior to removal of the aliquot. If the growth detection agent provides less accurate results after the microorganism strain cultures are treated, then this step will typically be performed after step 104, or at least after removal of the aliquot.

One suitable composition for treating cultures is a solvent such as an organic solvent and any combinations of organic solvents, including but not limited to ethyl acetate, dichloromethane, chloroform, decane, and any combinations thereof. Other compositions that are not expected to degrade the metabolite may be used, including compositions that may lyse the cells. Similarly, other compositions that solubilize the metabolite, particularly a less hydrophilic metabolite, but are not expected to degrade the metabolite may be used.

Another suitable composition that may be the same or different as the first suitable composition and used independently or in conjunction with the first composition is a composition that is able to chemically modify the metabolite as produced by the microorganism to allow or improve its detection in a high-throughput fluorescence polarization microorganism screening assay as described herein. For example, the metabolite as produced by the microorganism may be degraded or modified to include an additional functional group.

Treatment may include pelleting or other removal of large debris, such as intact cells, from the culture medium, particularly if such large debris may interfere with fluorescence detection.

Treatment in step 106 may exclude purification or substantial purification of the metabolite from the culture medium to allow its placement in a fluorescence polarization assay medium with a highly specific chemical composition.

Samples may be dried after treating, particularly if the composition used for treating will evaporate and may otherwise interfere with the fluorescence polarization assay. The metabolite of interest may be resolubilized in a suitable composition, such as an organic solvent, water, and any combinations of organic solvents and/or water.

In step 108, the amount of metabolite is assayed by adding a receptor and a fluorescent reporter to the sample representing a single compartment from the plurality of compartments and hence a single microorganism strain, then measuring fluorescence polarization. The fluorescent reporter is also able to bind the receptor. Fluorescence polarization is correlated with the amount of metabolite in the sample. The sample may be moved from the compartment in which the microorganism was cultured or from any intervening treatment, storage, or other compartments or containers to a multi-compartment fluorescence polarization assay device, such as a multi-well plate suitable for measuring fluorescence polarization. The multi-compartment assay device used in this fluorescence polarization assay may have at least as many compartments as the plurality of compartments used to culture the microorganism. In particular, it may have more compartments, allowing duplicate samples or different fluorescence polarization assay conditions to be tested from the same microorganism strain culture.

The receptor may be any molecule, such as protein, a DNA-based molecule, or an RNA-based molecule, for which metabolite binding is of interest. Suitable receptors may be generated de novo by computational design. Suitable receptors also include naturally occurring receptors and variants of naturally occurring receptors whose binding affinity for the fluorescent reporter and/or metabolite has been increased through directed evolution technologies, such as phage, mRNA, and yeast surface display technologies. The receptor may also be of a partially or wholly random sequence and selected for binding through directed evolution technologies, such as phage, mRNA, and yeast surface display technologies. The receptor may also be an antibody/monobody or fragments thereof, or an aptamer.

The fluorescent reporter may be any fluorescent molecule that competes with the metabolite for binding to the receptor, such that the amount of reporter unbound to the receptor in the well of the multi-well plate correlates with the amount of metabolite present that binds to the receptor. Both the receptor and the fluorescent reporter may be soluble in the culture medium contained in the compartment in which the microorganism was cultured.

The fluorescent reporter may include a small molecule chemically bound to a fluorescent molecule, such as a fluorophore-labeled small molecule. Suitable fluorophore classes include fluoresceins, rhodamines and cyanines. The fluorescent reporter is able to bind to the receptor and may be a derivative of the metabolite. The fluorescent reporter tumbles significantly more slowly when bound to the receptor than when the fluorescent reporter is not bound to the receptor. The significantly slower tumbling of the fluorescent reporter when bound to the receptor results in a significantly more polarized light emission upon absorption of polarized light than the light emission of the fluorescent reporter when unbound to the receptor. This difference in polarized light emission may be detected and discerned, for example using a spectroscopic detector coupled to a processor programmed with appropriate instructions or software.

The fluorescent reporter may include a chemical linker between the fluorescent moiety and the receptor-binding small molecule. However, a sterically large fluorescent molecule may decrease the binding affinity between the small molecule and the receptor. This may be mitigated by binding the fluorescent molecule at sites on the small molecule known or determined to not be crucial for receptor binding. Smaller fluorophores may also be used.

The length of a chemical linker may be selected to be within a certain range to ensure that fluorescent reporter/receptor binding remains at an acceptable level, but the tumbling of the fluorescent moiety is reduced when the fluorescent reporter is bound to the receptor. Suitable linkers include carbohydrate linkers such as oligomethylene linkers, containing at least one methylene or at least three methylenes and no more than twenty methylenes. Other linkers include polyethylene glycol containing at least one ethylene glycol or at least three ethylene glycol units and no more than ten ethylene glycol units. Other linkers include amino acid based linkers containing at least one amino acid or at least three amino acids and no more than ten amino acids. Other linkers include a combination of the above units. The linkers may be covalently linking the binding moiety of the fluorescent reporter with the fluorescent moiety of the fluorescent reporter. Such covalent linkage may be a carbonyl, a carbon-carbon bond, a carbon-heteroatom bond such as a carbon-nitrogen bond or a carbon-oxygen bond or a carbon-sulfur bond or a combination of such bonds.

Finally, fluorescent reporters with high quantum yield may be used for increasing fluorescent signal intensity and thus fluorescence polarization assay sensitivity.

Generating a fluorescent reporter that is a derivative of a small molecule, instead of generating a fluorescent receptor, as is the case in many other assays, may provide a simpler and quicker assay than those that rely on fluorescent receptors, such as assays using fluorophore quenching in the binding site. In addition, the fluorescence polarization assay described herein decouple fluorescence signal generation and metabolite binding to the receptor and thus are modular in contrast to assays in which those events are coupled, such as assays relying on transcription factor or riboswitches. Furthermore, the decoupling may facilitate modifications of the assay, as generating a new reporter and receptor is often simpler than creating an allosteric receptor.

The relative concentrations of the receptor and fluorescent reporter may be selected such that, if there is no metabolite able to bind the receptor present in a test sample, then most of the fluorescent reporter will be bound to a receptor. For example, at least 80%, at least 90%, or at least 95% of the fluorescent reporter will be bound to a receptor.

As metabolite concentration increases, the amount of fluorescent reporter bound to the receptor decreases. A standard curve may be prepared using known amounts of the same or a similar metabolite.

A high-throughput fluorescence polarization microorganism screening assay as described herein may be readily tunable to detect a range of metabolite concentrations by adjusting the concentration of various components of the assay such as the fluorescent reporter and the media. For instance, even with a given set of test samples, the receptor concentration can be increased over multiple rounds of high-throughput screening or in different high-throughput assay compartments to detect higher metabolite concentrations. Alternatively, with a given set of test samples, the sample may be diluted or concentrated over multiple rounds of high-throughput screening or in different high-throughput assay compartments so that the metabolite concentration in at least one assay well corresponding to a given test sample is more likely to fall within the detectable range.

In addition, a high-throughput fluorescence polarization microorganism screening assay as described herein may be readily tunable to detect a range of metabolite derivatives and/or metabolite concentrations by generating variants of the components of the assay, such as the receptor and the fluorescent reporter. Variant receptors and/or variant fluorescent reporters may result in different binding affinities and allow detection of various concentrations of metabolites. The concentration of metabolite derivatives in the assay may be detected by the use of receptor and fluorescent reporter variants.

In addition, for some high-throughput fluorescence polarization microorganism screening assays, an optimized concentration of fluorescent reporter to obtain a reliable fluorescence polarization signal may be known. For others, it may be empirically determined by testing various combinations of the receptor and fluorescent reporter concentrations until a reliable fluorescence polarization signal is obtained.

The lower sensitivity limit for a high-throughput fluorescence-polarization microorganism screening assay depends on the equilibrium dissociation constant ($K_d$) of the receptor and fluorescent reporter and the $K_d$ of the receptor and the metabolite. The assay may be used with fluorescent reporters having a $K_d$ of less than 1 mM, less than 500 µM, less than 100 µM, less than 50 µM, less than 10 µM, less than 5 µM, less than 1 µM, less than 500 nM, less than 100 nM, less than 20 nM, less than 10 nM, less than 5 nM, or less than 1 nm to detect metabolites, which may also bind to the receptor with any of these binding affinities as well. Tighter binding of both the fluorescent reporter and the metabolite to the receptor may provide more accurate results, although less tight binding may be accommodated by increasing the relative receptor concentration, but at some concentration, most receptors will exhibit protein aggregation or non-specific binding to the fluorescent reporter, which may cause inaccurate results. The binding affinities of the fluorescent reporter and the metabolite for the receptor may be similar, such as within one order of magnitude or two or three orders of magnitude of one another. Alternatively, the binding affinities of the fluorescent reporter and the metabolite for the receptor may differ, for example to allow tuning of the metabolite concentrations detectable.

Alternatively, a given cutoff metabolite concentration, which may be selected to correspond to a cutoff metabolite production level that designates a high-producing microorganism and the fluorescence polarization assay may be set up such that a selected amount, such as no more than 50%, no more than 10%, no more than 5%, no more than 1%, or no more than 0.5% of the fluorescent reporter is bound to the receptor at that cutoff metabolite concentration.

The overall performance of a fluorescence polarization screening assay may also be evaluated using statistical methods, such as calculation of the Z' score. The Z' score is a statistical parameter that takes into account the assay dynamic range and variability with measurements. The Z' score may be calculated using the following equation:

$$Z'=1-(3\sigma n+3\sigma p)/(\mu n-\mu p),$$

where σn is the standard deviation of a negative control, which may be a similar microorganism known to not produce the metabolite, σp is the standard deviation of a positive control, which may be a similar microorganism know to produce the metabolite, σn is the mean fluorescence polarization value for the negative control and σp is the mean fluorescence polarization value for the positive control.

Assay conditions may be adjusted or selected to achieve at least a selected Z' score. An ideal Z' score is 1. Any fluorescence polarization screening assay conditions that result in a Z' score of at least 0.7, at least 0.8, or at least 0.9 may be deemed sufficiently accurate for purposes of this disclosure.

In step 110, high-producing microorganism stains are identified. This identification is typically based on concentration of metabolite produced, concentration or total amount of metabolite produced per cell, which may be measured by the fluorescence polarization measurement and optionally also the cell density in the corresponding well of the multi-well culture. Identification may be based on a relative production amount, with, for example, the top 10%, top 5%, or top 1% of strains by concentration of metabolite produced or concentration of metabolite produced per cell being designated as high-producing. Alternatively, it may be based on a cutoff, with only strains producing at least a selected concentration of metabolite or selected concentration or amount of metabolite per cell designated as high-producing.

The metabolite may also be confirmed to be an expected metabolite, or, if there is no expected metabolite because the high-throughput fluorescence polarization microorganism screening assay is being used to detect new metabolites that bind to the receptor, microorganism strains with at least a selected concentration of metabolite or concentration or amount of metabolite per cell may be further studied to characterize the metabolite.

High-producing microorganism strains are typically already isolated for the high-throughput fluorescence polarization microorganism screening assay, but isolation may be confirmed, or the strains may be isolated and re-assayed, if needed. In either event, an isolated high-producing microorganism strain results.

In a variation of the above high-throughput fluorescence polarization microorganism screening assay, instead of different strains of the microorganism being represented in different compartments of the plurality of compartments used in step 102, different culture conditions for the same strain of microorganism may be represented in different compartments. The microorganisms may have been cultured under different conditions prior to introduction to the plurality of compartments, and in step 102 those different culture conditions may be maintained, or all samples may be placed in identical culture conditions once introduced to the plurality of compartments. Alternatively, the microorganisms may have been cultured under the same conditions prior to introduction to the plurality of compartments, and introduced to different culture conditions in step 102. Different culture conditions may in particular include different media, different culture additives, different salt types and concentrations, different carbon sources, different pH levels, different atmospheric components and pressure, different co-cultured organisms, different metabolic precursors, different ambient light levels, different aeration levels, different Carbon-Nitrogen ratios, different incubation time, different temperatures, different humidity levels, different plate material composition.

The information obtained in step 110 in this variation will then be the identification of high-producing culture conditions for the microorganism strain tested. Variations of culture conditions may include different culture media, different culture supplements, different culture temperatures, different culture atmospheres, different culture motions, such as shaking, and different durations of culture.

Because the robustness and growth capacity of the microorganism strain or culture conditions may also be of relevance to its potential uses, high-producing microorganism strains, high-producing culture conditions, or microorganism strains producing non-expected metabolites may further be characterized as high-growth or low-growth using cell density information from step 104, and low-growth microorganisms or culture conditions may be excluded, even if they are otherwise high-producing.

A high-throughput fluorescence polarization microorganism screening assay of the present disclosure may be used to identify high-producing microorganisms for known metabolites or their analogs, to identify new analogs of known metabolites or new metabolites, and to metabolically engineer high-producing microorganisms for metabolites.

In one example high-throughput fluorescence polarization screening assay, aspects of which are explained in further detail in the examples below, the receptor may be FKBP12.

The fluorescent reporter may be a fluorescently-labeled FKBP12-binding molecule, such as FK506 (tacrolimus), rapamycin (sirolimus), and/or meridamycin. The fluorescent label may be fluorescein. The metabolite may be a FKBP12-binding molecule, such as FK506 (tacrolimus), rapamycin (sirolimus), meridamycin, and/or their analogs. The microorganism screened may be metabolically engineered microorganism, such as a metabolically engineered *Streptomyces tsukubaensis* (*S. tsukubaensis*).

In another example of high-throughput fluorescence polarization screening assay, aspects of which are explained in further detail in the examples below, the receptor may be *E. coli* dihydrofolate reductase (eDHFR) and the fluorescent reporter may be a fluorescently-labeled eDHFR-binding molecule, such as trimethoprim (TMP). TMP selectively inhibits bacterial dihydrofolate reductase, a key enzyme in the folic acid pathway in bacteria that are obligate folic acid synthesizers.

In another example high-throughput fluorescence polarization screening assay, aspects of which are explained in further detail in the examples below, the receptor may be tetracycline receptor (TetR), which normally represses the transcription of tetracycline resistance genes in the absence of tetracycline, but allows their transcription in the presence of tetracycline. The fluorescent reporter or metabolite may be a TAN molecule chemically linked to a fluorescent molecule.

Other suitable receptor/fluorescent reporter combinations include penicillin binding proteins/penicillin, 5-HT/serotonin, adenine transferase/adenine, and estrogen receptor/estradiol, FKBP12/SLF; Cyclophilin 40/cyclosporin A (CsA); adiponectin/matairesinol, arctiin and gramine; cannabinoid/clonazepam, phenobarbital; dopamine/tetrandrine and aspartate transcarbamylase/ATP. In general, any binding protein/metabolite or binding-DNA or RNA/metabolite combinations may be used to detect a metabolite in the fluorescence polarization assay.

The present disclosure further provides materials for use in a high-throughput fluorescence polarization microorganism screening assay, including, but not limited to a microorganism strain to use as a control or as the starting strain for metabolic engineering, culture media or culture media components, such as rehydratable powder, standard metabolite samples with standard concentrations, multi-well plates or other devices with a plurality of compartments, media used to form a plurality of compartments, receptors, fluorescent reporters, fluorescent labels that may be attached to reporters, reagents used to attach fluorescent labels to reporters, growth detection agents, and compositions used to treat the cells to render any metabolites of interest available to bind to the receptor, if needed.

The present disclosure further includes a high-throughput fluorescence polarization microorganism screening assay kit containing at least two of the above materials or other reagents.

6. EXAMPLES

The presently disclosed subject matter will be better understood by reference to the following Examples, which are provided as exemplary of the invention, and not by way of limitation. For instance, the high-throughput fluorescence polarization microorganism screening assays described in detail in these examples are provided as proof-of-concept examples to demonstrate how such as assay may operate.

6.1 Example 1—FK506 High-Throughput Fluorescence Polarization Microorganism Screening Assay FK506 was selected as an example metabolite to demonstrate a high-throughput fluorescence polarization assay because it is naturally produced by *S. tuskubaensis*, because its ability to bind to the FKBP12 intracellular receptor is well-studied using low-throughput techniques, and because other small molecules able to competitively bind to FKBP12, in particular rapamycin (sirolimus), and meridamycin, are also well-studied. Furthermore, because FK506 has been a successful immunosuppressant drug, there is considerable interest in optimizing its production and in discovering additional analogs also able to bind to FKBP12.

The experiments described in this example, the entire process, from the onset of mutagenesis through screening took only twelve days, which was three times faster than a common low-throughput method for generating and screening a metabolically engineered *streptomyces* strain for rapamycin production using growth inhibition overlay assay on agar plates. Furthermore the high-throughput fluorescence polarization assay described below took only two hours of incubation time and can allow between $10^4$ and $10^5$ samples to be assayed per day on single plate reader.

Microorganism Mutation

*S. tsukubaensis* (NRRL 18488) was obtained from the Agricultural Research Service Culture Collection (NRRL), USA. NRRL 18488 was grown on inorganic salts/starch agar media (ISP4) (BD Difco, #277210) at 28° C. for 4 days to obtain spores. UV mutagenesis was performed using a Stratalinker 2400 (Agilent). UV dose was calibrated to obtain a 99% kill rate.

In particular, a *S. tsukubaensis* spore suspension was irradiated with UV (killing ratio of 99%) and plated on ISP4 agar. Sporulated colonies appeared after 3-4 days. These metabolically engineered strains were picked to create a glycerol spore stock in a 96-well plate. The glycerol stock plate was used to inoculate a recovery culture plate followed by assay plates to produce FK506 as described below.

Recovery Culture and Culture in Multi-Well Plates 2.2 mL, square, 96-well deep well plates (Axygen Scientific) were used to further culture the metabolically engineered *S. tsukubaensis* strains. A modified two-stage cultivation method was used. Recovery culture occurred in 500 µL of modified BaSa seed medium, which was inoculated with NRRL 18488 spores and incubated for 3 days at 28° C. and 250 rpm (Innova 44R, 2-inch orbit).

The recovery culture (10%) was used to inoculate 500 µL 750 µL, and 1000 µL of ISPz media per well in the 96-well deep well plates and incubated for 4-8 days at 28° C. and 250 rpm. All plates were sealed with two layers of sterile, breathable rayon seal (AeraSeal).

Cell Growth Measurements

Cell growth was initially determined by measuring the dry weight of the cells, taking into account submerged mycelia as well as growth on the walls above the liquid level. The cells were pelleted in pre-weighed 4 mL glass vials, washed twice with acid to remove insoluble $CaCO_3$ in the culture media, and then dried in an oven for 2 days before measuring the mass. For the construction of a standard curve, the cells were transferred onto pre-weighed Nalgene filter units (polyether sulfone, membrane diameter 75 mm, pore size 0.45 Thermo Scientific), washed twice with acidified water (pH 0.5) to remove insoluble $CaCO_3$ in the media, and then dried in an oven at 80° C. until constant weight (1 day) before measuring the mass.

Figure 2:
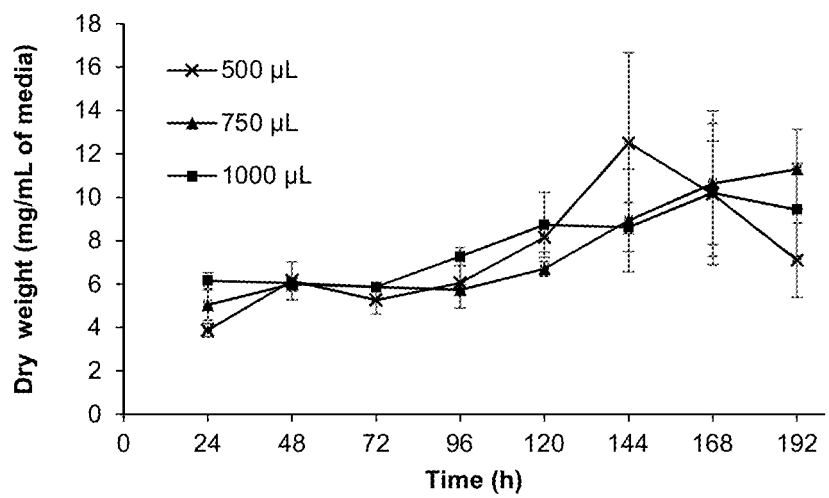
FIG. 2 is a graph of growth curves of metabolically engineered microorganisms grown in 500, 750 and 1000 μL of culture medium on a multi-well plate as measured by increase in dry mass over time.

This method, the results of which are presented in FIG. 2, resulted in large error bars due to the challenge of recovering all cell clumps/mycelia. Thus, a growth detection agent, methylene blue, was used to obtain more accurate results.

Each well of the 96-well deep well plates was assayed for cell growth at the end of the culture period. Cell growth was measured using a methylene blue absorption assay. 100 µL of methylene blue solution (final concentration of 1.5 mM) was added to 100 µL of sample in a separate Corning Costar polystyrene clear 96-well plate. The plate was incubated for 15 min at 80° C., and mixed every 5 minutes in a high-frequency microplate shaker (800 rpm, 10 s). The plate was centrifuged for 5 min at 3000 rpm and 10 µL of supernatant was mixed with 190 µL of water in a new plate. The absorbance was determined in a Tecan plate reader at 660 nm.

Figure 3:
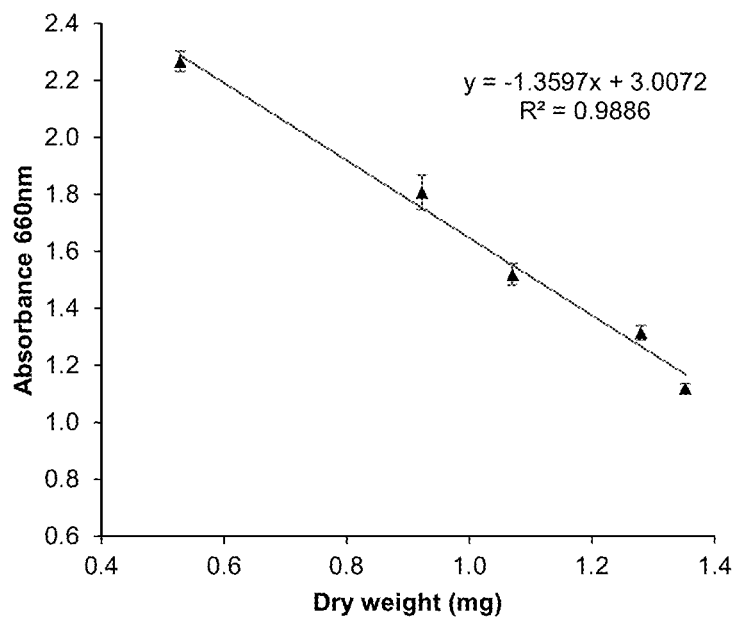
FIG. 3 is a standard curve of methylene blue absorbance (at 660 nm) against dry weight of microorganisms cells.

A standard curve for methylene blue (FIG. 3) was developed by performing the cell growth assay on samples with different known amounts of *S. tuskubaensis* cells (by dry weight). A linear relationship was observed, with the amount of methylene blue left unabsorbed in solution decreasing proportionally with an increasing amount of cells. In addition, cell growth assay required only a small aliquot of cells and took only a short time, 30 minutes. These features, along with the ability to use a multi-well plate makes it more amendable to high-throughput screening than measuring dry weight.

Treatment to Extract FK506

FK506 is not secreted and thus is normally not readily available in culture medium absent a treatment to extract it from cells. To extract FK506 from cell cultures, initially the culture in each well was transferred into a 2 mL microcentrifuge tube. An equal volume of ethyl acetate was added and the tube was vortexed for 30 min. After centrifugation for 5 minutes, the top ethyl acetate layer was transferred into a 4 mL glass vial and evaporated to dryness by rotary evaporation. An equal volume of methanol was added to dissolve any FK506 present for subsequent testing. This process was labor-intensive and not practical for high-throughput screening.

As a result, for high-throughput fluorescence polarization screening, FK506 was extracted within the same 96-well deep well plate that was used for culture. First, the cells in the plates were subjected to 3 freeze-thaw cycles, then 100 µL of culture was removed for the methylene blue assay described above. An equal volume of ethyl acetate was added to the remaining culture. The plates were sealed with a silicone mat (ImpermaMat, Axygen Scientific), wrapped with parafilm, and incubated for 1 hour at 20° C., 800 rpm in a high frequency plate shaker. The plates were then centrifuged for 5 minutes at 3000 rpm. 100 µL of the top ethyl acetate layer was gently transferred to a 96-well polypropylene plate (Greiner). The plate was evaporated to dryness in a chemical hood, and 100 µL of methanol was added to dissolve the extracted FK506. This was added directly into assay wells of another plate for the fluorescence polarization assay.

Figure 4:
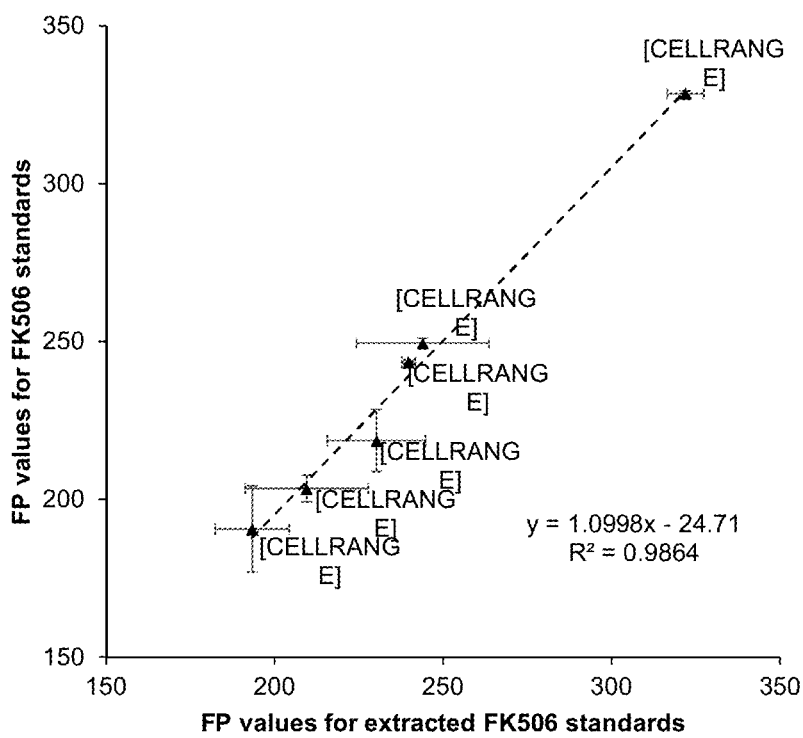
FIG. 4 is a graph of fluorescence polarization values for non-extracted FK506 standards versus extracted FK506 standards (in μM) extracted from media in 96-well plates; error bars are the standard deviation of 3 readings each of 2 replicate wells."

This methodology was first tested by spiking a series of FK506 standards into culture media without cells, followed by the extraction treatment described above. When later used in a fluorescence polarization assay as described below, the results matched those obtained using standards directly added to the fluorescence polarization assay (FIG. 4).

Fluorescence Polarization Assay

Figure 5:
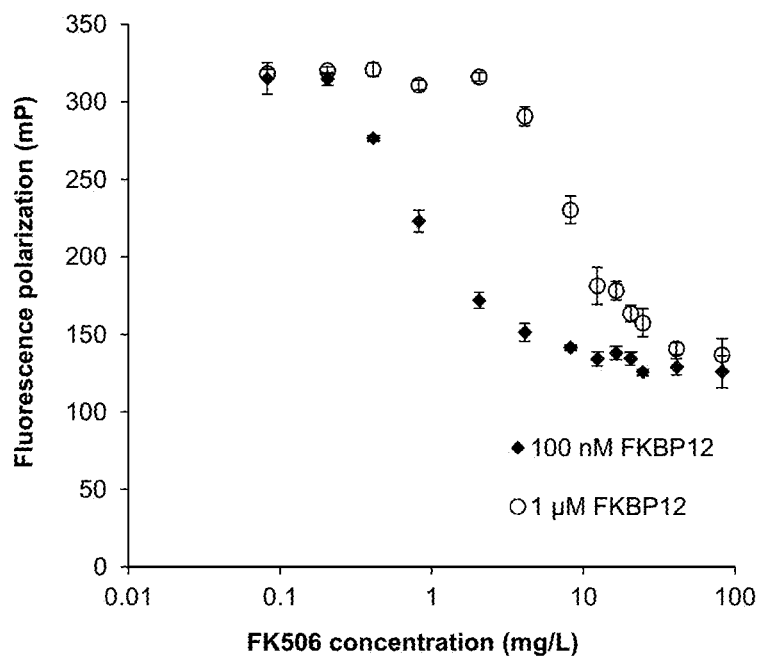
FIG. 5 is a standard curve generated using known amounts of FKBP12 receptor and FK506 fluorescent reporter; error bars represent standard deviations of three readings each for three replicate wells; concentrations refer to standard sample concentrations, final concentrations in the standard assay wells were ten times lower.

FK506 used to generate a standard curve for a fluorescence polarization assay was purchased from Sigma (#F4679). Mass spectrometry was performed using an LC-MS (Agilent 1100 Series Capillary LCMSD Trap XCT Spectrometer, NYU). A standard curve (FIG. 5) was generated by selected ion monitoring of ion counts at m/z of 826.4 (FK506+Na) using varying concentrations of commercial Sigma #F4679 and receptor concentrations of either 100 nM or 1 µM. The standard curve at both receptor concentrations was sigmoidal. At the 100 nM receptor concentration, it had a detection range of 0.1 mg/L to 10 mg/L and at the 1 µM receptor concentration, it had a detection range of 1 mg/L to 20 mg/L. These standard curves were used to determine the concentration of FK506 in the test samples.

The amount of FK506 produced by the test samples was quantified by both mass spectrometry and the FP assay.

The fluorescence polarization assay for FK506 in the test samples from the 96-well deep well plates was performed using FKBP12 (purified using the Ni-NTA kit (Qiagen) as a receptor and FK506-fluorescein (Ariad Pharmaceuticals) (Clackson et al., 1998; de Felipe et al., 2004) as a fluorescent reporter. The assay was performed in 384-well, round, black-bottomed plates (Corning #3821). A total volume of 40 µL per well was used. The final concentrations of reagents in each well were: 2.5 nM FK506-fluorescein and 1 µM FKBP12 (unless otherwise specified). The order of addition of each reagent into the well was: 32 µL of master mix containing FK506-fluorescein, 2× FP assay buffer (de Felipe et al., 2004) and water, followed by 4 µL of the sample (in methanol solvent) and finally 4 µL of 10 µM FKBP12. The plates were incubated for two hours before readings were taken (Victor X5 plate reader (Perkin Elmer), excitation filter (485 nm) and emission filter (535 nm)).

Figure 6:
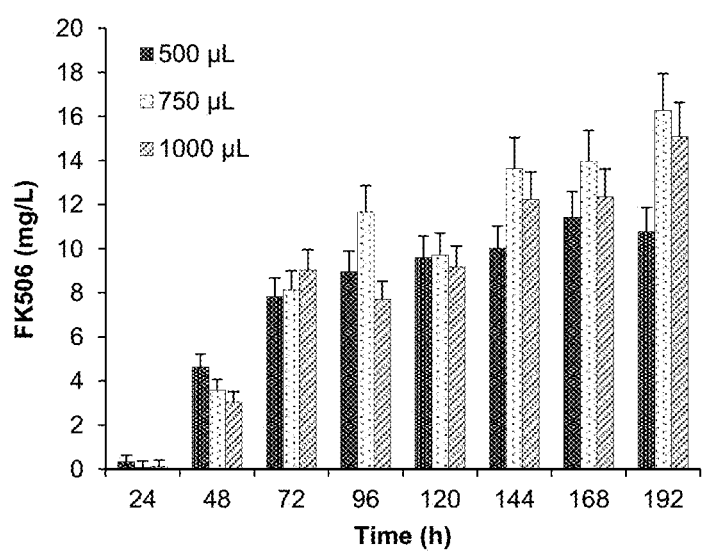
FIG. 6 is a graph of FK506 concentration (in mg per liter of culture media) over 8 days in samples of metabolically engineered microorganism strains cultured in a 96-well plate in 500, 750 and 1000 μL per well, as measured by a fluorescence polarization assay; all values were background subtracted based on wells containing the culture media alone.

Production of FK506 was observed after 24 h for all three volumes and increased over the course of 8 days (FIG. 6). Production levels as measured by the fluorescence polarization assay reached ~15 mg/L after 8 days for both 750 µL and 1000 µL cultures, which was higher than that for 500 µL culture (~11 mg/L) (FIG. 6).

The amount of FK506 in all test samples as measured by mass spectrometry and the fluorescence polarization assay was compared and found to correlate ($R^2$=0.705). Significantly, the fluorescence polarization assay displayed much lower variability as compared to the mass spectrometry measurements (FIG. 7).

160 strains from the metabolically engineered *S. tsukubaensis* library were then screened for FK506 production. Results are presented in FIG. 8, with strains arranged in order of productivity. These results are typical of what might be expected for a library of metabolically engineered microorganisms known to produce the metabolite of interest.

Overall the metabolically engineered library strains exhibits productivities that ranged from 47% to 160% of the unmutated strain. In general because the amount of cells (dry weight in g per mL of culture media, as estimated using methylene blue as described herein) was relative constant in all samples and did not vary with FK506 production, samples with higher concentrations of FK506 (mg/L, as measured using the fluorescence polarization assay) had higher productivities (mg of FK506/g of dry weight cell).

However, some samples, such as strain 43, had a high productivity value despite a lower FK506 concentration because the amount of cells was lower. Some samples, such as strain 119, were excluded from further analysis because they appeared to have high productivity, but the amount of cells was very low, indicating that the cells did not grow in the multi-well plate culture. This may have resulted from an experimental error, or growth impairment due to mutations. In such instances of low cell amounts, rescreening may be recommended so that the strain can be properly identified.

A model was used to determine which components of the fluorescence polarization assay may be modified in order to increase the dynamic range of the assay. This model is represented by the following equations:

$$KD_{PL} = \frac{[P][L]}{[PL]} \cong \frac{([P]_0 - [PL])([L]_0 - [PL])}{[PL]} \quad (1)$$

$$KD_{PC} = \frac{[P][C]}{[PC]} \cong \frac{([P]_0 - [PL])([C]_0 - [PC])}{[PC]} \quad (2)$$

$$[PL] = \frac{([P]_0 + [L]_0 + KD_{PL}) - \sqrt{([P]_0 + [L]_0 + KD_{PL})^2 - 4[P]_0[L]_0}}{2} \quad (3)$$

$$\frac{[PC]}{[PC]+[C]} = \frac{([P]_0 - [PL])}{KD_{PC} + ([P]_0 - [PL])} \quad (4)$$

For a receptor P, a metabolite L, a fluorescent reporter C, a metabolite-receptor complex PL, a fluorescent reporter-receptor complex PC, a $K_d$ of KDPL between P and L and a $K_d$ of KDPC between P and C, Equations 1 and 2 hold assuming $[P]_0 \gg [C]_0$. Equations 1 and 2 could be rearranged to Equations 3 and 4, respectively, assuming $[P]_0 \gg [C]_0$.

Predictions from this model were validated against actual assay results (FIG. 9).

The model suggests that modifying receptor concentration and the affinity of the receptor for the metabolite while maintaining high affinity of the receptor for the fluorescent reporter should provide a dynamic range of detection across six order of magnitude of metabolite concentration (FIG. 10).

Culture in Flasks

High-productivity metabolically engineered *S. tsukubaensis* strains were cultured in flasks by inoculating 4.5 mL of BaSa with 500 µL of spores and incubating for 40 h at 28° C. and 230 rpm. This culture was then used to inoculate 5 mL of ISPz production media (to a final OD600 of 1) in 50 mL, unbaffled flasks (Pyrex Erlenmeyer 50 mL, CE-FLAS050), and incubated for 8 days at 28° C. and 230 rpm.

On average, the strains identified as high-productivity using the high-throughput fluorescence polarization assay produced higher concentrations of FK506 per gram of cells than the non-mutated *S. tsukubaensis* parent strain (WT) and had higher productivities. (FIG. 11). *S. albus*, which does not produce FK506, was also cultured as a control. Repetition of the flask production three times, with three flasks per strain showed that production yields of all strains was highly variable. This further establishes that culture in multi-well plates, which exhibited no such high production variability, prior to fluorescence polarization screening may be more accurate and useful than culture in flasks.

Calculation of Z' Score

The Z' score as described by Zhang et al., 1999, A Simple Statistical Parameter for Use in Evaluation and Validation of High Throughput Screening Assays. Journal of biomolecular screening. 4, 67-73, was calculated for the high-throughput fluorescence polarization screening assay using the following equation: Z'=1−(3σn+3σp)/(µn−µp), where σn is the standard deviation of the negative control (*S. albus*, which does not produce FK506), σp is the standard deviation of the positive control (M71—a metabolically engineered *S. tsukubaensis* strain exhibiting increased FK506 production), σn is the mean fluorescence polarization value for *S. albus* and μp is the mean fluorescence polarization value for M71.

Using the fluorescence polarization assay as described above, 96 wells of *S. albus* and 96 wells of the M71 metabolically engineered *S. tsukubaensis* strain were evaluated. Results are presented in FIG. 12. A Z' score of 0.81 was calculated, which is sufficiently high for the fluorescence polarization assay to be deemed highly accurate.

6.2 Example 2—High-Throughput Fluorescence Polarization Assay for Other FKBP12-Binding Metabolites Several metabolites other than FK506 are known to bind the FKBP12 receptor, including rapamycin and meridamycin. Accordingly, fluorescence polarization assay standard curves were generated as described above in connection with FK506 for rapamycin (FIG. 13) and meridamycin (FIG. 14), establishing that these metabolites may also be used in the fluorescent reporter or detected as a metabolite in a high-throughput fluorescence polarization microorganism screening assay as described herein.

6.3 Example 3—High-Throughput Fluorescence Polarization Assay for *E. coli* Dihydrofolate Reductase-Binding Metabolites In another high-throughput fluorescence polarization screening assay, stable, monomeric eDHFR was used as the receptor and TMP linked at the 4'-carboxy position to the bright, photostable fluorophore TAMRA was used as the fluorescent reporter. A 4'-position derivatization was chosen because biochemical characterizations have shown that TMP and its 4'-methoxy substituted esters have comparable DHFR affinities. Using a fluorescence polarization assay similar to that described in Example 1 above, TMP was detected at concentrations of 0.5 μM to 5 μM (FIG. 15), which is within the range of common metabolite titers obtained from metabolically engineered microorganisms. Trimethoprim was also detected by the fluorescent polarization assay in spiked yeast growth media (FIG. 16).

6.4 Example 4—TetR Fluorescence Polarization Assay

Receptor and Fluorescent Reporter

A Histidine-tagged TetR class B (TetR(B)) was overexpressed and purified from *E. coli* for use as the receptor in a high-throughput fluorescence polarization assay. Its activity was verified using an independent fluorescence assay. TetR is a homodimeric protein.

Inspection of the high-resolution structure of TetR bound to tetracycline derivatives as well as biochemical characterization suggested that tetracycline could be derivatized at the D ring without disrupting binding to TetR. Accordingly, the fluorescent reporter was synthesized by attaching a fluorophore to the D-ring of commercially available 9-aminominocycline. An alternative linker or a fluorophore of a different size, charge, or photophysical properties were not tested, but may be used to optimize the fluorescence polarization assay.

Tetracycline Assay

Doxycycline, which binds to TetR, was used as a metabolite in a fluorescence polarization assay with TetR(B) and a minocycline-fluorescein fluorescent reporter. Results are shown in FIG. 17. Each assay well contains 1.5 μM TetR(B), 100 nM minocycline-fluorescein in a buffer of pH 7.0 with 50 mM Na3PO4, 100 mM NaCl, 5 mM MgCl2, 1 mM EDTA, and 1 mM DTT. Doxycycline (Tc) in 25% dimethylsulfoxide was added to a final concentration of 5% dimethyl sulfoxide. All wells were done in triplicate with error bars representing standard errors.

Doxycycline Assay

Tetracycline, which also binds to TetR, was used as a metabolite in a fluorescence polarization assay with TetR(B) and a minocycline-fluorescein fluorescent reporter. Results are shown in FIG. 18. Each assay well contains 300 nM TetR(B), 100 nM minocycline-fluorescein in a buffer of pH 7.0 with 50 mM Na3PO4, 100 mM NaCl, 5 mM MgCl2, 1 mM EDTA, and 1 mM DTT. Tetracycline (Tc) in 0.5% dimethylsulfoxide was added to a final concentration of 0.1% dimethyl sulfoxide. All wells were done in triplicate with error bars representing standard errors.

Detection of Multiple Tetracycline Analogs

Oxytetracycline, anhydrotetracycline, tetracycline, doxycycline, minocycline which bind to TetR, were used as metabolites in a fluorescence polarization assay with TetR (B) and a fluorescent reporter. Trimethoprim and no ligand were used as negative controls. Results are shown in FIG. 19. Each assay well contains 300 nM TetR(B), 100 nM minocycline-fluorescein in a buffer of pH 7.0 with 50 mM Na3PO4, 100 mM NaCl, 5 mM MgCl2, 1 mM EDTA, and 1 mM DTT. Trimethoprim (TMP), Anhydrotetracycline hydrochloride (Atc), Tetracycline (Tc), Doxycycline hydrochloride (Dox), Oxytetrayycline (Oxy-Tc), and minocycline hydrochloride (min) or 0.5% dimethyl sulfoxide control were added to a final concentration of 0.1% dimethyl sulfoxide. All wells were done in triplicate with error bars representing standard errors.

Detection of Tetracycline in Complex Media

Tetracycline was detected by a fluorescence polarization assay from spiked *S. lividans* cultures. Cultures were spiked with tetracycline, filtered and fluorescence polarization was measured in the presence of TetR(B) and a minocycline-fluorescein fluorescent reporter (FIG. 20). A culture of *Streptomyces lividans* was partitioned into five fractions. Four fractions were spiked with different concentrations of Tetracycline (Tc) in 10% methanol (150 μM, 15 μM, 150 nM, 15 nM Tc). The fifth fraction was not spiked, and remained a negative control. All fractions were filtered through a 0.2 um syringe filter. The resulting culture was treated as a competitive inhibitor for the TetR(B) and min-F system to final concentrations of 30 μM, 3 μM, 30 nM, 3 nM, 0 nM tetracyclinec-spiked media, 2% methanol, 300 nM TetR(B), 100 nM minocycline-fluorescein and buffer composition of pH 7.0 with 50 mM Na3PO4, 100 mM NaCl, 5 mM MgCl2, 1 mM EDTA, and 1 mM DTT. All wells were done in triplicate with error bars representing standard errors.

We claim:

1. A method of high-throughput fluorescence polarization microorganism screening comprising:
   culturing a plurality of microorganism strains that produce a metabolite in a plurality of separate compartments to produce a plurality of samples;
   adding a receptor and fluorescent reporter to the plurality of samples obtained from the plurality of compartments;
   detecting fluorescence polarization of the reporter in the plurality of samples in a multi-compartment fluorescence polarization assay device, wherein fluorescence polarization of the reporter correlates inversely with a concentration of the metabolite in any given sample because the metabolite competes with the fluorescent reporter to bind to the receptor and binding of the fluorescent reporter to the receptor increases fluorescence polarization;

calculating concentration of the metabolite in at least a portion of the plurality of samples; and designating at least one of the plurality of microorganism strains as high-producing or low-producing based on the calculated concentration of metabolite for at least one sample.

2. The method of claim 1, wherein the plurality of separate compartments comprise wells on a multi-well plate.

3. The method of claim 1, wherein the multi-compartment fluorescence polarization assay device comprises a multi-well plate.

4. The method of claim 1, wherein the plurality of separate compartments used in culturing are the same as a plurality of compartments in the multi-compartment fluorescence polarization assay device used in detecting fluorescence polarization.

5. The method of claim 1, wherein the multi-compartment fluorescence polarization assay device comprises more compartments than the plurality of separate compartments used in culturing.

6. The method of claim 5, wherein the plurality of samples include duplicate samples obtained from the same compartment used in culturing, and wherein each of the duplicate samples is located in a separate compartment of the multi-compartment fluorescence polarization assay device.

7. The method of claim 5, wherein at least a portion of the plurality of samples are diluted to different dilutions, and wherein each dilution is located in a separate compartment of the multi-compartment polarization assay device.

8. The method of claim 5, wherein at least two different concentrations of receptor or fluorescent reporter are added to different samples from the same compartment used for culture in at least a portion of the plurality of samples, and wherein each dilution is located in a separate compartment of the multi-compartment polarization assay device.

9. The method of claim 1, further comprising varying a concentration of the receptor or varying a concentration of the fluorescent reporter to detect a different concentration of metabolite or a different metabolite.

10. The method of claim 1, wherein the microorganism comprises a bacteria.

11. The method of claim 1, wherein the microorganism comprises a fungus.

12. The method of claim 11, wherein the microorganism comprises a yeast.

13. The method of claim 1, wherein the microorganism comprises an algae.

14. The method of claim 1, wherein the microorganism is present as individual cells small, unorganized clumps of cells due to a stage in the microorganism's life cycle or due to culture conditions.

15. The method of claim 1, wherein the microorganism comprises a recombinant microorganism.

16. The method of claim 1, wherein the microorganism comprises a non-recombinant microorganism.

17. The method of claim 1, wherein the microorganism comprises a metabolically engineered microorganism.

18. The method of claim 17, further comprising producing the plurality of metabolically engineered microorganism strains by subjecting a microorganism to ultraviolet radiation.

19. The method of claim 1, further comprising assaying microorganism growth in at least a portion of the plurality of samples.

20. The method of claim 19, further comprising assaying microorganism growth in a separate multi-compartment device than the multi-compartment fluorescence polarization assay device.

21. The method of claim 19, wherein designating at least one of the plurality of microorganism strains as high-producing or low-producing is also based on the assayed microorganism growth.

22. The method of claim 19, wherein assaying microorganism growth comprises adding a growth detection agent to a plurality of growth samples corresponding to the plurality of samples, then detecting the growth detection agent in the plurality of growth samples.

23. The method of claim 1, further comprising treating the plurality of samples to render the metabolite accessible to bind to the receptor, for example by freeze-thaw methods, by adding solvent, and/or by adding a detergent.

24. The method of claim 1, wherein the receptor comprises a protein.

25. The method of claim 1, wherein the receptor comprises a DNA-based molecule or an RNA-based molecule.

26. The method of claim 1, wherein the fluorescent reporter comprises a small molecule able to bind to the receptor and a fluorescent molecule.

27. The method of claim 26, wherein the fluorescent molecule comprises a fluorescein, a rhodamine, or a cyanine.

28. The method of claim 19, further comprising generating a standard curve for use in assaying microorganism growth.

29. The method of claim 1, further comprising generating a standard curve correlating metabolite concentration and fluorescence polarization for the metabolite for use in calculating concentration of the metabolite.

30. The method of claim 1, wherein at least $10^2$ separate wells each containing one of the plurality of microorganism strains are assayed per day.

31. The method of claim 1, wherein the metabolite and fluorescent reporter have binding affinities for the reporter within one order of magnitude from one another.

32. The method of claim 1, wherein the metabolite or the fluorescent reporter or both have an equilibrium dissociation constant ($K_d$) with respect to the receptor of less than 1 mM.

33. The method of claim 1, wherein the method of high-throughput fluorescence polarization microorganism screening has a Z' score of at least 0.70.

34. The method of claim 1, wherein the reporter comprises FKBP12, the fluorescent reporter comprises FK506 (tacrolimus), rapamycin (sirolimus), meridamycin, SLF, their analogs, and any combinations thereof.

35. The method of claim 34, wherein the metabolite comprises FK506 (tacrolimus), rapamycin (sirolimus), meridamycin, SLF, their analogs, and any combinations thereof.

36. The method of claim 34, wherein the microorganism comprises *Streptomyces tsukubaensis*.

37. The method of claim 1, wherein the receptor comprises *E. coli* dihydrofolate reductase (eDHFR), the fluorescent reporter comprises trimethoprim (TMP), it analogs, and any combinations thereof.

38. The method of claim 37, wherein the metabolite comprises trimethoprim (TMP), it analogs, and any combinations thereof.

39. The method of claim 1, wherein the receptor comprises tetracycline receptor (TetR), and the fluorescent reporter comprises a TAN molecule, its analogs, and any combinations thereof.

40. The method of claim 39, wherein the metabolite comprises a TAN molecule, its analogs, and any combinations thereof.

41. The method of claim 1, wherein the receptor comprises a penicillin binding protein; 5HT; adenine transferase; estrogen receptor; cyclophilin; adiponectin; cannabinoid; domapine; or asparate transcarbamylase, and the fluorescent reporter comprises, respectively penicillin, its analogs, and any combinations thereof; serotonin, its analogs, and any combinations thereof; adenine, its analogs, and any combinations thereof; estradiol, its analogs, and any combinations thereof; cyclosporin A (CsA), its analogs, and any combinations thereof; matairesinol, arctiin, gramine, their analogs, and any combinations thereof; clonazepam, phenobarbital, their analogs, and any combinations thereof; tetrandrine its analogs, and any combinations thereof; and adenosine triphosphate (ATP) its analogs, and any combinations thereof.

42. The method of claim 41, wherein the metabolite comprises, respectively penicillin, its analogs, and any combinations thereof; serotonin, its analogs, and any combinations thereof; adenine, its analogs, and any combinations thereof; estradiol, its analogs, and any combinations thereof; cyclosporin A (CsA), its analogs, and any combinations thereof; matairesinol, arctiin, gramine, their analogs, and any combinations thereof; clonazepam, phenobarbital, their analogs, and any combinations thereof; tetrandrine its analogs, and any combinations thereof; and adenosine triphosphate (ATP) its analogs, and any combinations thereof.

43. A method of high-throughput fluorescence polarization microorganism screening comprising:
   culturing a microorganism strain that produces a metabolite under plurality of different culture conditions in a plurality of separate compartments to produce a plurality of samples;
   adding a receptor and fluorescent reporter to the plurality of samples obtained from the plurality of compartments;
   detecting fluorescence polarization of the reporter in the plurality of samples in a multi-compartment fluorescence polarization assay device, wherein fluorescence polarization of the reporter correlates inversely with a concentration of the metabolite in any given sample because the metabolite competes with the fluorescent reporter to bind to the receptor and binding of the fluorescent reporter to the receptor increases fluorescence polarization;
   calculating concentration of the metabolite in at least a portion of the plurality of samples; and
   designating at least one of the plurality of culture conditions as high-producing or low-producing based on the calculated concentration of metabolite for at least one sample.

44. The method of claim 43, wherein at least two of the plurality of culture conditions comprise different culture media, different culture supplements, different culture temperatures, different culture atmospheres, different culture motions, such as shaking, different durations of culture, and any combinations thereof.

* * * * *